US00PP30490P2

(12) United States Plant Patent
Nicolaï

(10) Patent No.: US PP30,490 P2
(45) Date of Patent: May 14, 2019

(54) APPLE TREE NAMED 'ZOUK 31'

(50) Latin Name: *Malus domestica*
Varietal Denomination: ZOUK 31

(71) Applicant: Zouk B.V.B.A., Sint-Truiden (BE)

(72) Inventor: Johan Nicolaï, Sint-Truiden (BE)

(73) Assignee: Zouk B.V.B.A., Sint-Truiden (BE)

( * ) Notice: Subject to any disclaimer, the term of this patent is extended or adjusted under 35 U.S.C. 154(b) by 0 days.

(21) Appl. No.: 15/732,499

(22) Filed: Nov. 20, 2017

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875; A01H 5/08; A01H 5/02; A01H 5/0222; A01H 6/7418
See application file for complete search history.

(56) References Cited

U.S. PATENT DOCUMENTS

PP4,121 P * 10/1977 ten Hove ..... Plt./162
PP6,450 P 12/1988 Visser
PP6,955 P 8/1989 Kiddle
PP16,559 P3 5/2006 Nicolai
PP17,201 P3 11/2006 Nicolai
PP25,671 P3 7/2015 Kellerhals
2004/0025211 P1 2/2004 Zulch

OTHER PUBLICATIONS

Fresh Plaza Feb. 15, 2016 Johan Nicolai presents new early Gala variety, retrieved on Oct. 16, 2018, retrieved from the Internet at http://www.freshplaza.com/article/2153468/johan-nicolai-presents-new-early-gala-variety/, 2 pp. (Year: 2016).*
U.S. Appl. No. 15/732,496, "Apple Tree Named 'Zouk 16'," filed Nov. 20, 2017, for inventor Johan Nicolai and for applicant Zouk B.V.B.A.
U.S. Appl. No. 15/732,497, "Apple Tree Named 'Zouk 32'," filed Nov. 20, 2017, for inventor Johan Nicolai and for applicant Zouk B.V.B.A.
U.S. Appl. No. 15/732,502, "Apple Tree Named 'Zouk G1'," filed Nov. 20, 2017, for inventor Johan Nicolai and for applicant Zouk B.V.B.A.
Guerra (2017). "Strains improve standard varieties translated and edited by Julia Strobl," European Fruit Network Jun. 2017, retrieved on Oct. 22, 2018 from the Internet at http://kp.eufrin.eu/fileadmin/user_upload/documents/804-14df1cca1323ccb72d8b027c37356dfd.pdf, pp. 14-17.
Horticulture Week (2015). "Apple varieties found by chance unveiled at show," retrieved on Oct. 22, 2018 from the Internet at https://www.hortweek.com/apple-varieties-found-chance-unveiled-show/fresh-produce/article/1370357, 2 pp.

* cited by examiner

*Primary Examiner* — June Hwu
(74) *Attorney, Agent, or Firm* — Morrison & Foerster LLP

(57) ABSTRACT

A new and distinctive variety of a *Malus domestica* apple tree, named 'ZOUK 31' that is distinguished by its medium-sized tree with short feathers and a dark green leaf-color that produces yellow fruit having a pink-gold blush, is disclosed.

4 Drawing Sheets

Latin name:
Botanical classification: *Malus domestica.*
Varietal denomination: The varietal denomination of the claimed apple tree variety is 'ZOUK 31'.

BACKGROUND OF THE INVENTION

Apples are an economically important crop. Accordingly, there exists a need to develop new varieties of apple tree with improved characteristics, such as disease resistance.

BRIEF SUMMARY OF THE INVENTION

In order to meet these needs, the present invention is directed to an improved variety of apple tree. In particular, the invention relates to a new and distinct variety of apple tree (*Malus domestica*), which has been denominated as 'ZOUK 31'.

Apple tree variety 'ZOUK 31' was discovered in in Sint-Truiden, Belgium as a hybrid from a controlled pollination cross of seed parent 'Rubinstep' (unpatented) and pollen parent 'Delblush' (U.S. Plant Pat. No. 10,276). The original seedling of the new variety was first asexually propagated by T-budding and bench grafting onto 'M9 T337' (also known as 'M9 NAKBT337' or 'M9'; unpatented) rootstock, 'MM106' (also known as 'Malling-Merton 106'; unpatented) rootstock, and 'MM111' (also known as 'Malling-Merton 111'; unpatented) rootstock in 2013 and subsequently planted in a nursery bed for tree production.

The original 'ZOUK 31' tree and its progeny have been observed growing in a plot located in Gorsem, Belgium. The new variety produces fruit that matures for commercial harvesting approximately at the end of September in the Haspengouw area in Belgium.

The 'ZOUK 31' apple tree variety is distinguished from other apple tree varieties by the following unique combination of characteristics: the new variety is a medium-sized tree with short feathers and a dark green leaf-color that produces yellow fruit having a pink-gold blush. The 'ZOUK 31' apple tree variety was selected for the distinctive aroma of its fruit that is very different from the aroma of the fruit of existing varieties, for the firm to very firm texture of its fruit, and for the very good shelf life of its fruit.

Asexual reproduction of the 'ZOUK 31' apple tree variety by T-budding and bench grafting onto 'M9 T337', 'MM106' and 'MM111' rootstocks in Sint-Truiden, Belgium shows that the foregoing and all other characteristics and distinctions are true to type and are established and transmitted through succeeding asexual propagations.

BRIEF DESCRIPTION OF THE DRAWINGS

The 'ZOUK 31' apple tree variety is illustrated by the accompanying photographs hick show fruit of the tree, as well as flowers. The colors shown are as true as can be reasonably obtained by conventional photographic procedures. However, the colors in the photographs may vary with lighting conditions and, therefore, color characteristics of this new variety should be determined with reference to the observations described herein, rather than from the photographs alone. The photographs are from trees that are four years old.

FIG. 4A illustrates unopened flowers (i.e., flower buds) of apple tree variety 'ZOUK 31'. FIG. 4B illustrates flowers of apple tree variety 'ZOUK 31'.

DETAILED BOTANICAL DESCRIPTION

Figure 1:
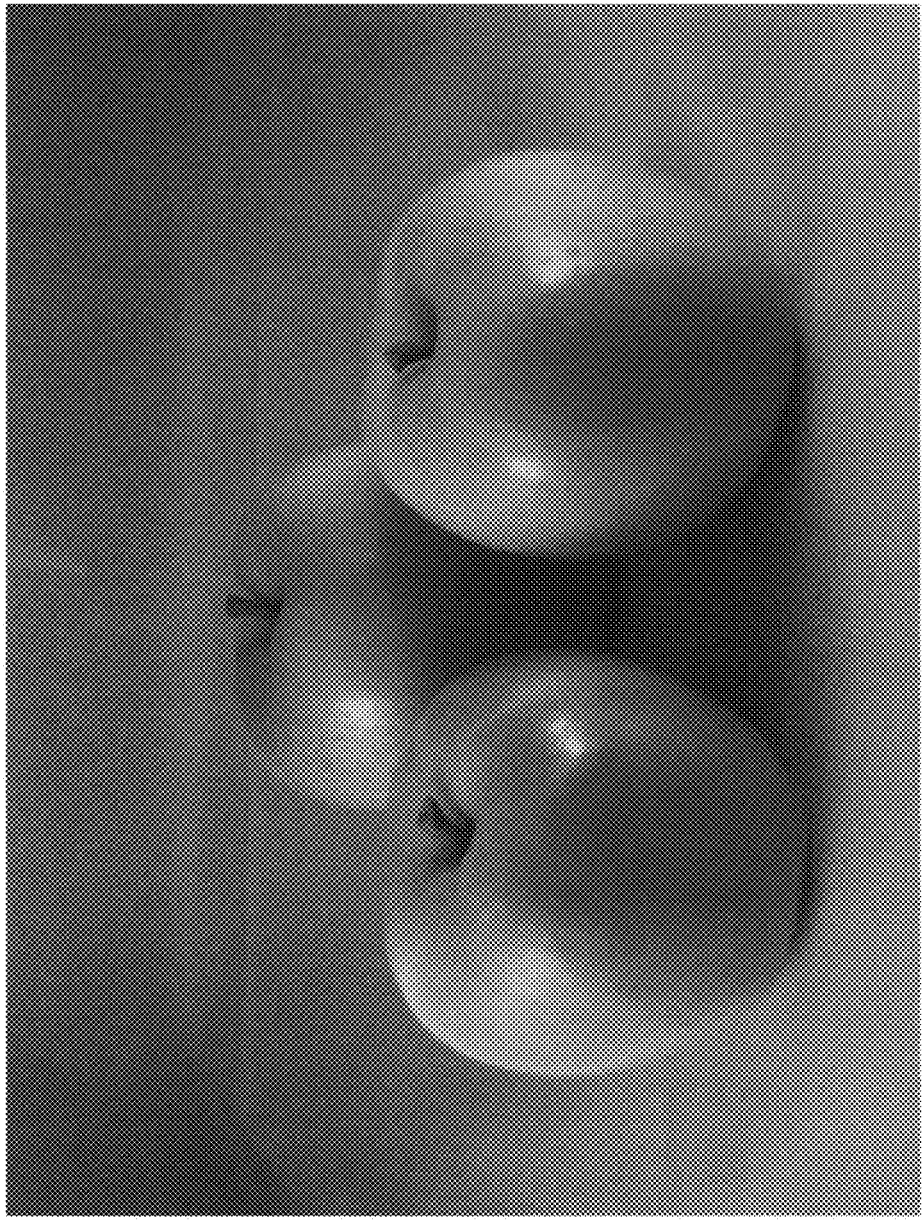
FIG. 1 illustrates fruit of apple tree variety 'ZOUK 31'.
Figure 2:
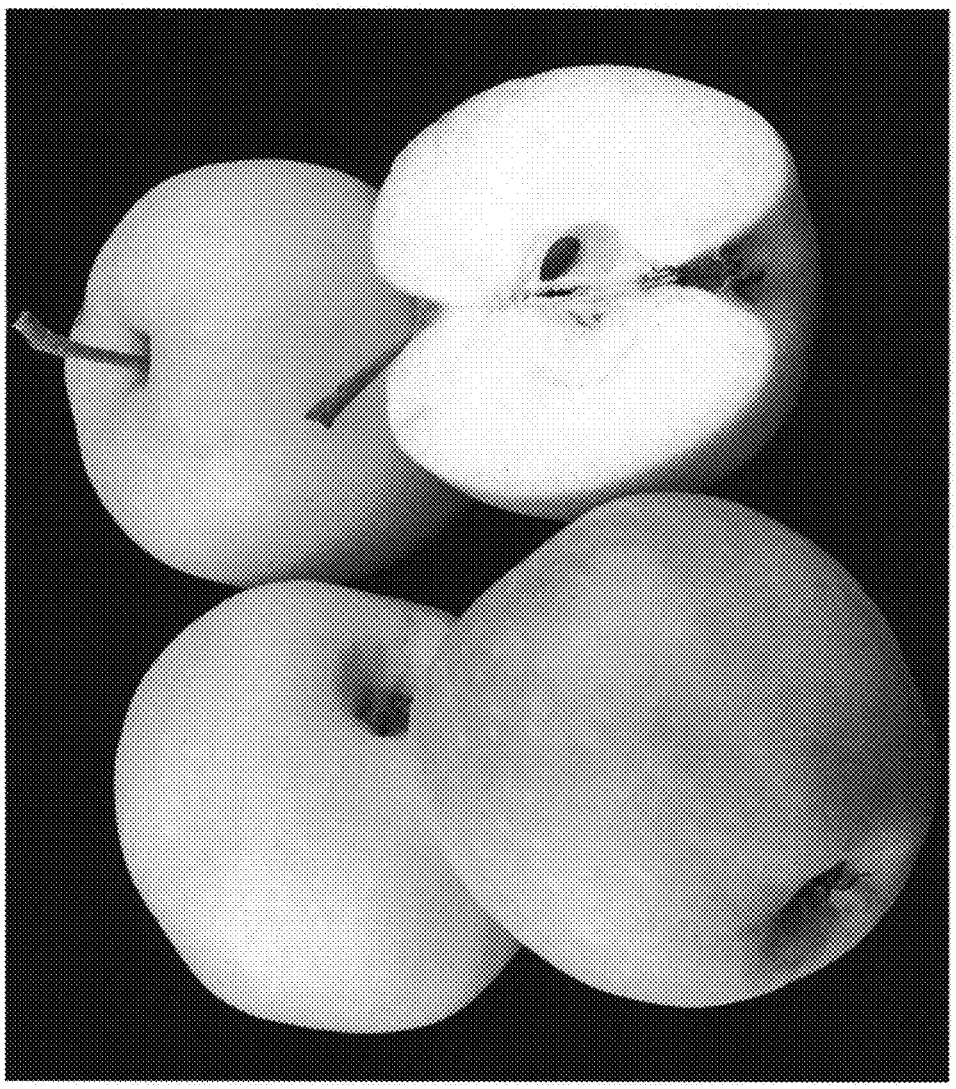
FIG. 2 illustrates fruit of apple tree variety 'ZOUK 31' cut in half to view the inside flesh of the fruit.
Figure 3:
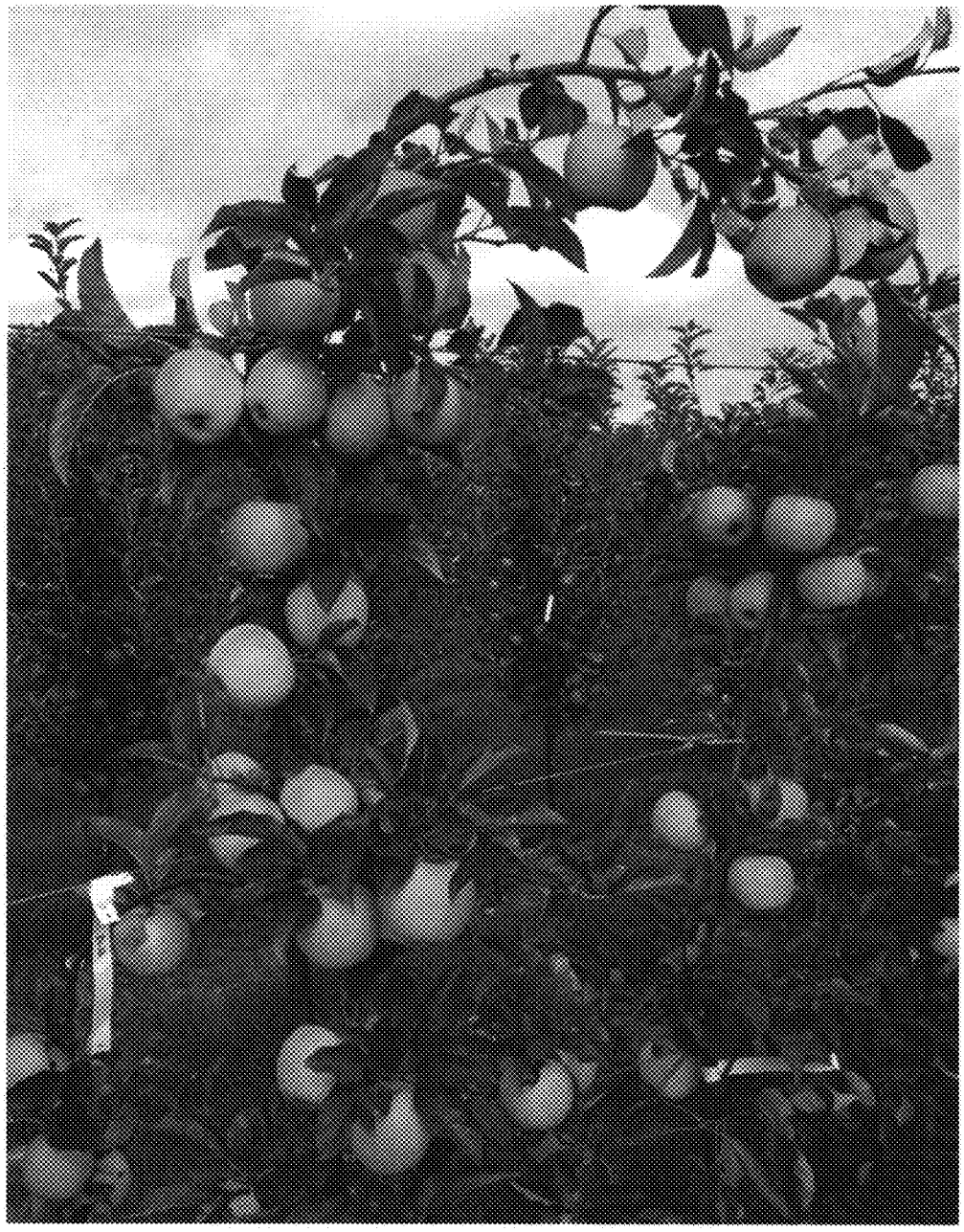
FIG. 3 illustrates a tree of apple tree variety 'ZOUK 31' with fruit on the tree (colored side).
Figure 4B:
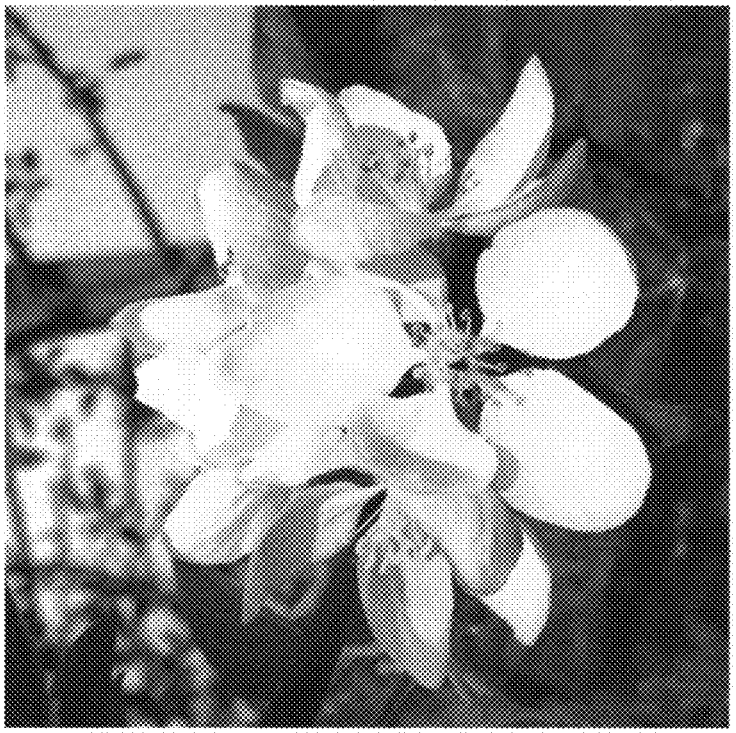
FIGS. 4A and 4B illustrate flowers of apple tree variety 'ZOUK 31' at different developmental stages.
Figure 4A:
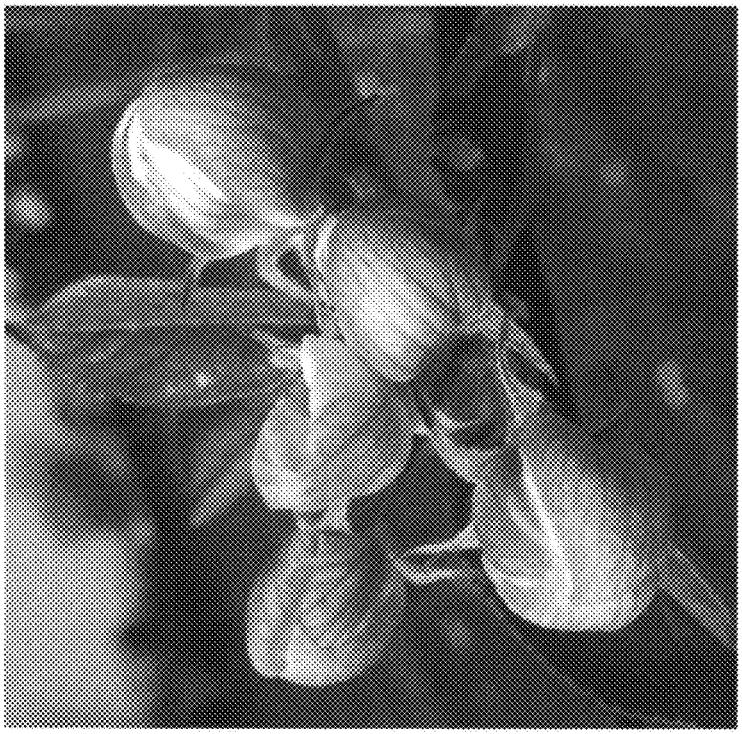

The following description sets forth the distinctive characteristics of 'ZOUK 31'. The following botanical description of 'ZOUK 31' is based on observations of the originally identified tree, and asexually reproduced progeny, grown on 'M9 T337' rootstock in Sint-Truiden, Belgium. Referring more specifically to the details of the new and distinct variety of apple tree, unless otherwise stated, the following has been observed on trees that were four years of age growing on 'M9 T337' rootstock in Sint-Truiden, Belgium. Numbers provided are averages of data measured from the sampling trees.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. All color references are from The R.H.S. Colour Chart of The Royal Horticultural Society of London (R.H.S.) (Sixth Edition, 2015).

Tree:

*Vigor.*—Medium, with a strong apical dominance (comparable to 'Golden Delicious' (unpatented)).

*Overall shape.*—Spreading.

*Height.*—Approximately 3.00 m.

*Width.*—Approximately 1.30 m.

*Caliper.*—Approximately 40 mm at 50 mm above the graft union.

*Trunk bark texture.*—Smooth with raised, prominent lenticels.

*Trunk bark color.*—About greyed-green (RHS 198B).

*Patches or other markings.*—No prominent spots or scales evident.

*Primary branches.*—Fine; branches emerge at an angle of approximately 60 to approximately 90 degrees with branches higher in the tree emerging at approximately 60 degrees. Measured trees are grown to a central leader system. The typical and observed lateral branch length is 100 cm (first primary branch above graft union and arising from main stem).

*Branch color.*—One-year old branches are moderate reddish brown (RHS 166B), while older branches are brownish grey (RHS N200B).

*Branch lenticels.*—Medium density, approximately 5 per square centimeter. Shape: Oval. Color: Yellowish-white (RHS 156D). Size: Approximately 1.2 mm long by approximately 0.9 mm wide.

*Internodes.*—Average internode length is approximately 3.5 cm for a 1-year old shoot.

*Bearing.*—Annual.

*Hardiness.*—European Zone 8 hardy (comparable to 'Royal Gala' (U.S. Plant Pat. No. 4,121) and 'Golden Delicious' (unpatented)).

*Disease resistance.*—Moderate tolerance to apple scab caused by the fungus *Venturia inaequalis* (more tolerant to apple scab than 'Golden Delicious' (unpatented) and 'Delblush' (U.S. Plant Pat. No. 10,276), and less tolerant to apple scab than 'Rubinstep' (unpatented)).

Leaves:

*Texture.*—Upper leaf surface: Leathery. Lower leaf surface: Smooth.

*Sheen.*—Upper leaf surface: Medium glossy. Lower leaf surface: Not glossy.

*Length.*—Average 106 mm.

*Width.*—Average 59 mm.

*Margin.*—Serrate.

*Base shape.*—Obtuse to rounded.

*Tip shape.*—Acute.

*Stipules.*—2 present on 90% of leaves. Where present, opposite, slender.

*Leaf color.*—Upper leaf surface: About dark green. Lower leaf surface: Silver-green.

*Leaf vein color.*—Light green-yellowish.

*Pubescence.*—Upper leaf surface: Absent to very fine. Lower leaf surface: Fine (light).

*Petiole length.*—Average 38 mm.

*Petiole color.*—Moderate yellow green (RHS 139C).

Flower:

*General.*—Size. — Medium. Diameter: Average 40 mm (when spread out on a flat surface). Shape. — Ovoid to round.

*Flower bud.*—Size. — Average about 12 mm long. Shape. — Rounded, becoming more elongated and slightly acute just before opening. Color. — Unopened bud: Strong purplish red (RHS 64C). Opened bud: White (RHS NN155D) with streaks of pale purplish pink (RHS 62D).

*Petals.*—Numbers of petals per flower. — 5. Length. — 20 mm. Width. — 11 mm. Shape. — Ovate. Base: Acuminate. Apex: Rounded. Arrangement. — Separate but overlapping. Color. — Upper petal surface: White (RHS NN155D) with streaks of pale purplish pink (RHS 62D). Lower petal surface: About white (RHS N155D) to moderate purplish pink (RHS 62B).

*Sepals*.—Number. — About 5 per flower. Length. — 10 mm. Width. — 2 mm. Color. — About green (RHS 143A), tinged at the tip with about red-purple (RHS 59A). Arrangement. — Arranged separately.

*Pedicel/peduncle*.—Apples do not have branched inflorescences and hence do not have pedicels. The flower stalk of an apple is the peduncle. Length. — 22.5 mm. Diameter. — 1 mm. Color. — Strong yellow-green (RHS 143C).

*Stamen*.—Number. — Approximately 20 per flower, arranged in a row around the circumference of the receptacle. Length. — 7 mm. Filament color. — Greenish white (RHS 155C). Anthers. — About 20 per flower. Anther Color: Pale yellow green (RHS 4D), Unopened anther color: About yellow (RHS 5D). Pollen color. — Light greenish yellow (RHS 4B).

*Pistil*— .—Stigma length. — 5 to 6 mm. Position of the stigmas in relation to the anthers. — Above. Styles. — Fused. Color. — Green-yellow.

*Pollination requirements*.—Later flowering varieties, e.g., 'Granny Smith' (unpatented) or 'Golden Delicious' (unpatented), will overlap sufficiently in flowering to enable pollination.

*Fragrance*.—Slight.

*Time of beginning of flowering*.—End of April, beginning of May in Sint-Truiden, Belgium.

*Bloom season*.—In 2016 in Sint-Truiden, Belgium, full bloom was on the $9^{th}$ of May.

Fruit:

*General*.—Measurements are the average of 10 typical 'ZOUK 31' apples.

*Size*.—Medium. Length. — Approximately 71.0 mm. Width. — Approximately 70 mm on the upper side, tapering toward the bottom. Shape: — Conical. The calyx is very slightly open (on average 0.5 mm). Cavity. — Width: Approximately 10 mm. Depth: Approximately 7 mm. Basin. — Shape: Concave. Width: Approximately 18 mm. Depth: Approximately 7 mm.

*Fruit stem*.—Length. — Approximately 22.5 mm. Diameter. — Approximately 2.8 mm. Color. — Brownish-orange (RHS 164A).

*Locules*.—5 slightly open locules with seeds free of the carpel wall at maturity.

*Fruit skin*.—Tendency to crack. — Absent. Thickness. — Medium. Surface texture. — Glossy and smooth. Lenticels. — Present, Diameter: Approximately 0.5 to 1.0 mm. Color: Generally green in color (RHS 129A). Density: Average of about 5 lenticels/$cm^2$. Color. — General color effect: Brilliant greenish yellow (RHS 6C). Ground color: At maturity, brilliant greenish yellow (RHS 6C). Over color: Dependent on climatic conditions; in a very hot climate (e.g., Spain), there is practically no over color and the fruit is completely yellow (RHS 6C), i.e., solid flush; in a more moderate climate (e.g., Belgium), there is an orange over color ranging from light orange (RHS 28C) to vivid orange (RHS 28B) like a blush that is flushed and mottled. Russetting around the stalk attachment and eye basin. — Absent. Bloom. — Weak. Stripes. — Absent.

*Fruit flesh*.—Flavor. — Strong aromatic flavor, fresh and juicy with a good balance between sweet and sour. Brix. — Average approximately 15 Brix. Juiciness. — Very juicy. Color. — Pale yellow (RHS 8D). Aroma. — Strong. Firmness. — Firm to very firm.

*Core*.—Shape. — Round to slightly elongate. Diameter. — 20 mm. Length. — 23 mm. Number of bundles. — Approximately 10 per fruit. Calyx tube length. — 4 mm.

*Seed*.—Number. — About 2 to 3 seeds per cell. Shape. — Oval. Length. — 8 mm. Width. — 3 mm. Color. — Moderate brown (RHS 165A). Time of fruit eating maturity. — In 2018 in Sint-Truiden, Belgium, around the $14^{th}$ of September. In general, the time of fruit eating maturity is comparable to 'Golden Delicious' (unpatented) in Western Europe.

*Fruit production*.—First picking date in the 2015 season at Sint-Truiden, Belgium, was about the $28^{th}$ of September.

*Storage*.—Fruit remains fresh at room temperature (approximately 20° C.) for approximately 15 days, and can be stored up to approximately six months in cold storage (about 1° C. or about 34° F.).

*Shipping quality*.—Excellent, since the fruit is firm to very firm.

*Productivity*.—About 18 kg of fruit per plant for a 4-year-old-tree.

*Usage*.—Fresh eating.

COMPARISONS TO PARENTAL AND RELATED KNOWN VARIETIES

The 'ZOUK 31' apple tree variety is distinguished from its seed parent 'Rubinstep' (unpatented) in that fruit of 'ZOUK 31' matures approximately two weeks later than fruit of 'Rubinstep'. In addition, 'ZOUK 31' produces fruit that has a brilliant greenish yellow color with an over color that is dependent on climatic conditions (completely yellow in a hot climate; light orange to vivid orange in a moderate climate), whereas 'Rubinstep' produces fruit that has a bright orange-red color on a yellow-green background.

The 'ZOUK 31' apple tree variety is distinguished from its pollen parent 'Delblush' (U.S. Plant Pat. No. 10,276) in that 'ZOUK 31' produces fruit that is brilliant greenish yellow with an over color that is dependent on climatic conditions (completely yellow in a hot climate; light orange to vivid orange in a moderate climate), whereas 'Delblush' produces fruit that is deep yellow with an orange overcolor. Moreover, fruit of 'ZOUK 31' shows no tendency to bruising and russeting, while fruit of 'Delblush' is sensitive to bruising and slight russeting. Therefore, fruit of 'ZOUK 31' is much smoother than fruit of 'Delblush'.

Ten typical apples of 'ZOUK 31' and of 'Delblush' were obtained on Jan. 23, 2017 from trees growing near to one another, and tested for certain characteristics. Table 1 below compares the characteristics of apple tree variety 'ZOUK 31' with apple tree variety 'Delblush'. Column 1 lists the characteristics, column 2 shows the characteristics for apple tree variety 'ZOUK 31', and column 3 shows the characteristics for apple tree variety 'Delblush'. 'ZOUK 31' fruit firmness of 8.3 kg/$cm^2$ can be quantified as firm to very firm.

TABLE 1

| Characteristic | 'ZOUK 31' | 'Delblush' |
|---|---|---|
| Firmness (pressure kg/cm$^2$) | 8.3 | 5.9 |
| Moisture (weight of the juice extracted compared to the total weight of the fruit) | 14.6 | 10.9 |
| Soluble solids (in percent) | 15.4 | 14 |
| Malic acidity (g/l) | 5.6 | 5.9 |

The 'ZOUK 31' apple tree variety is distinguished from related known variety 'Nicoter' (U.S. Plant Pat. No. 17,201) in that 'ZOUK 31' produces fruit that has a brilliant greenish yellow color with an over color that is dependent on climatic conditions (completely yellow in a hot climate; light orange to vivid orange in a moderate climate), whereas 'Nicoter' produces fruit that has a bright red to dark red color on a green-yellow background.

What is claimed is:

1. A new and distinct variety of apple tree named 'ZOUK 31' as shown and described herein.

* * * * *